United States Patent [19]

Johan et al.

[11] 3,964,971

[45] June 22, 1976

[54] METHOD FOR INCREASING THE VITAMIN $B_{12}$ PRODUCTION IN FERMENTATION PROCESSES CARRIED OUT WITH METHANOBACTERIA

[75] Inventors: Béla Johan; László Szemler; János Fülöp; Tamas Szontagh; Emilia Simonovits née Czink; Judit Bekes nee Erdös; László Kuti; Robert Torös; Dénes Szekely; Lászlo Szabo; Károly Seitz; Tádé Vajda; Erzsébet Kovacs née Komoroczy; Anikó Hargital nee Franyo; Károly Polinszky, all of Budapest, Hungary

[73] Assignee: Richter Gedeon Vegyeszeti Gyar Rt., Budapest, Hungary

[22] Filed: Oct. 24, 1974

[21] Appl. No.: 517,797

[30] Foreign Application Priority Data

Oct. 26, 1973  Hungary.................................. RI 523

[52] U.S. Cl............................. 195/28 VB; 195/115
[51] Int. Cl.²............................................. C12D 5/06
[58] Field of Search ........................ 195/28 VB, 115

[56] References Cited
UNITED STATES PATENTS 3,062,724   11/1962   Reusser................................ 195/115

FOREIGN PATENTS OR APPLICATIONS 1,242,515   5/1968   U.S.S.R. .......................... 195/28 VB

*Primary Examiner*—Alvin E. Tanenholtz
*Attorney, Agent, or Firm*—Karl F. Ross; Herbert Dubno

[57] ABSTRACT

The invention relates to a method for increasing the vitamin $B_{12}$ production of fermentation processes performed in a known way with a mixed population of mesophilic methane-producing bacteria under anaerobic conditions. According to the invention in an enrichment period of preferably 4 to 7 days a nutrient concentrate containing mainly inorganic ammonium compounds as nitrogen source and mainly methanol as carbon source and having a N:C weight ratio of 1:10 to 1:20, preferably 1:11 to 1:15 is added in daily portions to a fermentation broth obtained from a usual vitamin $B_{12}$ fermentation process and containing living bacterium populations so as to increase the total concentration of assimilable nitrogen by a factor of maximum 4 until the end of the enrichment period, and thereafter the fermentation is terminated and the obtained fermentation broth with an increased vitamin $B_{12}$ content is processed, or the fermentation is continued by periodically removing a portion of the fermentation broth and supplementing it with a same volume of fresh nutrient medium containing mainly inorganic ammonium compounds as nitrogen source and mainly methanol as carbon source and having a N:C weight ratio of 1:10 to 1:20, preferably 1:11 to 1:15.

By this process fermentation broths with as high vitamin $B_{12}$ concentration as 40.000 mcg./l. can be obtained.

1 Claim, No Drawings

METHOD FOR INCREASING THE VITAMIN $B_{12}$ PRODUCTION IN FERMENTATION PROCESSES CARRIED OUT WITH METHANOBACTERIA

This invention relates to a method for increasing the vitamin $B_{12}$ production in fermentation processes carried out with methanobacteria. According to the new process of the invention fermentation broths containing at least 15.000 mcg./l. of vitamin $B_{12}$ are produced by cultivating a mixed mesophilic methane-producing microorganism population under anaerobic septic conditions in the presence of known nutrient components and precursors.

As known, vitamin $B_{12}$ is generally produced either by monocultural fermentation carried out under sterile conditions or with a mixed bacterium population of sewage sludge origin, adapted to a special culture medium (see Austrian Pat. No. 266 311). Several methods are known for increasing the vitamin $B_{12}$ yields of fermentations carried out with methane-producing mixed bacterium populations, but these methods can usually be applied to the production of fermentation broths which contain at most only about 10.000 mcg./l. of vitamin $B_{12}$.

The aim of the present invention is to elaborate an economical process for increasing the yield of vitamin $B_{12}$ in the usual fermentation processes utilizing known, semicontinuously maintained bacterium populations of sewage sludge origin.

It is known that the bacterium concentration of a fermentation broth (g. of dry biomass per liter of fermentation broth) can be increased primarily by increasing the amount of the bacterium mass. It is also known that the amount of the obtained bacterium mass depends, besides several other microbiological and biochemical factors, on the period required by the formation of the cell mass. One of the most important processes of the formation of cell mass is the biosynthesis of cell proteins; this biosynthesis is provided by the self-reproducing ability of the cells in the presence of the carbon, nitrogen and energy sources required for the biosynthesis.

In our previous investigations we have found that there is a strict correlation between the methanol metabolism, the cell growth and the vitamin $B_{12}$ production in fermentation (see L. L. Szemler and A. D. Szekely: Process Biochemistry, December 1969). Upon the effect of the dehydrogenase enzyme methanol is, in part, converted into an intermediate form of the cell substance or is oxidized into formic acid and carbon dioxide, respectively, while the other part is able to accept hydrogen which arises from the metabolism of the cells. The latter process, wherein methanol is reduced into methane, produces energy for the fermentation system, and the microbiological utilization of the energy promotes the biosynthesis of cell materials and vitamin $B_{12}$.

We have found furthermore that the propagation of the methane-producing mixed microorganism population requires the presence of an inorganic nitrogen source, more particularly an inorganic ammonium salt.

It also follows from the above that in the biosynthesis of amino acids and polypeptides the intermediate substance of the oxidation of methanol acts as a carbon source, the redox process is the source of energy, whereas the inorganic ammonium salts enter the process as nitrogen sources through enzymatic reactions.

Now we have found that the formation of the intermediate substance of the oxidation of methanol which acts as the carbon source in the fermentation process, as well as the utilization of the inorganic ammonium compounds serving as the nitrogen sources reach the desired optimum level only if the weight ratio of the nitrogen and carbon, present as inorganic ammonium compounds and as methanol, respectively, is between 1:10 and 1:20, preferably between 1:11 and 1:15 in a nutrient medium containing mainly inorganic ammonium salts as the nitrogen source and methanol as the carbon source. At these ratios the amount of the biomass formed in the fermentation broth and the concentration of the resulting vitamin $B_{12}$ are also maximum. Thus we have found that if the nutrient medium contains the other necessary components (e.g. inorganic salts and precursors) in sufficient amounts, the attainable concentration of vitamin $B_{12}$ depends essentially only on the concentration and the weight proportions of the above two components, i.e. the nitrogen in the inorganic ammonium salt and the carbon in the methanol.

If the amount of the ammonium nitrogen present in the nutrient broth is increased further with respect to the amount of methanol carbon, i.e. the weight ratio becomes higher than the optimum upper limit given above, the pH of the fermentation broth increases, whereas if the amount of methanol carbon is increased with respect to that of the ammonium nitrogen, the pH decreases. Both processes affect unfavourably the production of vitamin $B_{12}$.

The further experiments carried out with nutrient media containing inorganic ammonium nitrogen and methanol carbon as major components in the optimum weight ratios given above indicated that with such nutrient media the production of vitamin $B_{12}$ can be increased considerably and the concentration of vitamin $B_{12}$ can be increased to about 40.000 mcg./l. (i.e. by a factor of about four as compared to the known processes using nutrient media with the usual concentrations) simply by increasing substantially the total assimilable nitrogen and carbon concentrations of the fermentation broth by the addition of nutrients which contain increased amounts of inorganic ammonium compounds as the nitrogen source and methanol as the carbon source. The data of Table 1 indicate the correlation between the increased total nitrogen and carbon concentrations (provided by the gradual addition of nutrient media containing ammonium nitrogen and methanol carbon in a weight ratio between 1:11 and 1:15), and the production of vitamin $B_{12}$. The initial nitrogen and carbon concentrations as well as the initial concentration of vitamin $B_{12}$ given in the Table correspond to that obtainable by the known process of Hungarian Pat. No. 159 356.

Table 1

| Total amount of N | C | Attainable vitamin $B_{12}$ concentration, mcg./l. |
|---|---|---|
| in the fermentation broth mcg./l. | | |
| 1,000 | 2,500 | 10,000 to 11,000 |
| 1,150 | 3,800 | 11,000 |
| 1,250 | 4,300 | 12,000 |
| 1,350 | 4,600 | 13,000 |
| 1,450 | 5,000 | 14,000 |
| 1,550 | 5,450 | 15,000 |
| 1,650 | 5,650 | 16,000 |
| 1,750 | 6,150 | 17,000 |
| 1,850 | 6,450 | 18,000 |

Table 1-continued

| Total amount of N in the fermentation broth mcg./l. | C | Attainable vitamin $B_{12}$ concentration, mcg./l. |
|---|---|---|
| 1,000 | 2,500 | 10,000 to 11,000 |
| 1,950 | 6,750 | 19,000 |
| 2,050 | 7,100 | 20,000 |
| 2,150 | 7,350 | 21,000 |
| 2,250 | 7,550 | 22,000 |
| 2,350 | 8,000 | 23,000 |
| 2,450 | 8,425 | 24,000 |
| 2,550 | 8,800 | 25,000 |
| 2,650 | 9,210 | 26,000 |
| 2,750 | 9,520 | 27,000 |
| 2,850 | 10,000 | 28,000 |
| 2,950 | 10,350 | 29,000 |
| 3,050 | 10,700 | 30,000 |
| 3,150 | 11,100 | 31,000 |
| 3,250 | 11,420 | 32,000 |
| 3,350 | 11,750 | 33,000 |
| 3,450 | 12,000 | 34,000 |
| 3,550 | 12,320 | 35,000 |
| 3,650 | 12,710 | 36,000 |
| 3,750 | 13,050 | 37,000 |
| 3,850 | 13,380 | 38,000 |
| 3,950 | 13,730 | 39,000 |
| 4,050 | 14,060 | 40,000 |

The correlation given in Table 1 is generally valid when the nutrient media contain mainly inorganic ammonium nitrogen and methanol carbon, consequently the data listed in Table 1 give a simple and safe possibility to install any desired production level of vitamin $B_{12}$ between 10,000 and 40,000 mcg./l. for continuous and semicontinuous fermentation processes as well, simply by adjusting the nitrogen and carbon concentrations of the fermentation broth to the value corresponding to the desired level of vitamin $B_{12}$ production. This is accomplished by the gradual addition of a nutrient medium, containing the required amounts of ammonium nitrogen and methanol carbon in a weight ratio between 1:10 and 1:20, preferably between 1:11 and 1:15, to the fermentation broth.

Once the desired nitrogen and carbon concentrations of the fermentation broth and thus, simultaneously, the desired level of vitamin $B_{12}$ production has been reached as described above, this high level of vitamin $B_{12}$ production can be maintained for any desired period by performing continuous or semicontinuous fermentation, provided that the necessary nitrogen and carbon concentrations are maintained during the total period by the subsequent addition of fresh nutrient media in the appropriate amounts and compositions.

Thus, according to the invention, one proceeds as follows:

The starting medium may be a fermentation broth obtained in any of the known methanobacterial fermentation processes using conventional mixed methane-producing bacterium populations and containing about 10,000 mcg./l. of vitamin $B_{12}$. In this fermentation broth the total nitrogen and carbon concentrations are increased to the values corresponding to the desired vitamin $B_{12}$ production, as given in Table 1, by the gradual addition of a nutrient medium which contains, besides the usual components, inorganic ammonium compounds as the nitrogen source and methanol as the carbon source in amounts corresponding to an N:C ratio of 1:10 to 1:20, preferably 1:11 to 1:15. In parallel with the addition of this nutrient medium the concentration of vitamin $B_{12}$ also increases in the fermentation broth as indicated in Table 1, until the desired value is reached.

Now the obtained fermentation broth can be processed, and vitamin $B_{12}$ can be separated as a concentrate or as a pure product, or the fermentation can be continued in continuous or semicontinuous manner, and the high production level can be maintained steadily for any desired period by continuously removing a portion (as usual, daily 10%) of the fermentation broth and adding a fresh nutrient medium with the same volume and similar composition to the residue. Owing to the substantially increased production of vitamin $B_{12}$, attainable according to the process of the invention, it is also possible to remove a much higher daily amount of fermentation broth (e.g. about 20% daily, preferably in two or more portions, in comparison with the usual removal of 10% daily) for processing and to replace it with a fresh nutrient medium of the same volume.

Accordingly, during the increase of the vitamin $B_{12}$ production to the desired level as described above (enrichment period), a concentrated nutrient mixture, containing only a small amount of water, is added to the fermentation broth for 4 to 7 days. This nutrient mixture contains, besides the usuall additives (such as inorganic salts, 5,6-dimethylbenzimidazole, etc.), assimilable nitrogen mainly (i.e. at least 90%) in the form of inorganic ammonium compounds and assimilable carbon mainly (at least 90%) in the form of methanol, and the weight ratio of these two components (ammonium nitrogen, g./methanol carbon, g.) should be between 1:10 and 1:20, preferably between 1:11 and 1:15. During this enrichment period no fermentation borth is removed from the fermenter.

The daily amount of said nutrient medium to be introduced during the enrichment period must be chosen so that at the end of the enrichment period the total nitrogen content of the fermentation broth should reach the value corresponding to the desired vitamin $B_{12}$ concentration, as given in Table 1. When the N:C ratios of the nutrient mixture administered daily is maintained between the above values, at the end of the enrichment period the carbon content of the fermentation broth will also reach approximately the value given in Table 1 (a substantial part of the added carbon source leaves the system as methane gas).

At the end of the enrichment period the semicontinuous production of vitamin $B_{12}$ can be started wherein the concentration of vitamin $B_{12}$ attained in the enrichment period is preserved at a steady level in the fermentation broth removed periodically for processing. Accordingly, a part (in the usual method about 10% of the total volume) of the fermentation broth is removed daily from the fermenter and passed to processing, and the same volume of fresh nutrient broth is added to the remainder.

In order to maintain the attained level of production for practically any desired period, the nutrient medium added in the semicontinuous process must also contain nitrogen (mainly as inorganic ammonium compound) and carbon (mainly as methanol) in a ratio between 1:10 and 1:20, preferably 1:11 and 1:15. We have found, however, that in order to ensure the stability of the production level it is advantageous to adjust the methanol content of the nutrient broth added in the semicontinuous fermentation stage to an even higher value, i.e. to increase the ammonium nitrogen:methanol carbon ratio by about 6 to 10% with respect to that in the nutrient broth added in the enrichment period. This increase corresponds practically to about one unit, that is if in the enrichment period a nutrient broth with an ammonium nitrogen:methanol carbon ratio of e.g. 1:12 was used, a nutrient broth with a ratio of 1:13 is applied in the production stage.

The absolute amount of the fresh nutrient medium to be added daily should be sufficient to supplement completely the total amount of nitrogen removed in the form of fermentation broth daily from the fermenter. The total nitrogen content of the removed fermentation broth can be determined by known analytical measurements, e.g. according to the Kjeldahl method. The required daily supplement of methanol can be calculated from the prescribed ratio of ammonium nitrogen to methanol carbon.

The portion of the fermentation broth removed daily may be about 10% of the total broth, as in the usual processes, but the 2–4-fold increase in the vitamin $B_{12}$ content of the fermentation broth, attained according to the process of the invention, enables one to remove substantially larger portions of fermentation broth as well. Thus, for instance, about 20% of the fermentation broth can be removed daily for processing, preferably in two or more portions at appropriate intervals, and replaced always by the same volume of fresh nutrient broth with the above composition.

Thus, in accordance with the invention it is possible to maintain the high vitamin $B_{12}$ level of the fermentation broth, attained in the enrichment stage, for a practically unlimited time during the subsequent continuous or semicontinuous fermentation, and to perform a continuous, increase production by the continuous or periodical removal of fractions of the fermentation broth. The fermentation can, however, also be terminated after reaching the desired concentration of vitamin $B_{12}$, i.e. at the end of the enrichment period, ad the total mass of the fermentation broth, containing vitamin $B_{12}$ in the desired high amount, can be processed in a known manner to prepare vitamin $B_{12}$ concentrates or pure vitamin $B_{12}$.

Accordingly, the present invention relates to a method for increasing the vitamin $B_{12}$ production of fermentation processes performed in a known way with a mixed population of mesophilic methane-production bacteria under anaerobic conditions, in which in an enrichment period of preferably 4 to 7 days a nutrient concentrate containing mainly inorganic ammonium compounds as nitrogen source and mainly methanol as carbon source and having a N:C weight ratio of 1:10 to 1:20, preferably 1:11 to 1:15 is added in daily portions to a fermentation broth obtained from a usual vitamin $B_{12}$ fermentation process and containing living bacterium populations so as to increase the total concentration of assimilable nitrogen by a factor of maximum 4 until the end of the enrichment period, and thereafter the fermentation is terminated and the obtained fermentation broth with an increased vitamin $B_{12}$ content is processed, or the fermentation is continued by periodically removing a portion of the fermentation broth and supplementing it with the same volume of fresh nutrient medium containing mainly inorganic ammonium compounds as the nitrogen source and mainly methanol as the carbon source and having a N:C weight ratio of 1:10 to 1:20, preferably 1:11 to 1:15.

When the fermentation is continued, either semicontinuous or continuous methods can be applied. In the former case larger amounts (e.g. 10% of the total volume) of the fermentation broth are removed at appropriate intervals, e.g. once or twice a day and replaced by fresh nutrient medium, whereas in the latter case small portions of the fermentation broth are removed continuously and replaced by fresh nutrient broth.

The composition of the nutrient broth used in the process of the invention and the compositions in the known processes for producing vitamin $B_{12}$ (see e.g. Austrian Pat. No. 266 311) differ only in that the former contains as the nitrogen source mainly (i.e. at least 90%) inorganic ammonium compounds, such as ammonium phosphate, ammonium sulfate, ammonium hydroxide, etc., and as the carbon source mainly (i.e. at leat 90%) methanol, and the N:C weight ratio in the nutrient broth is between 1:10 and 1:20, preferably between 1:11 and 1:15. In addition to these main components the nutrient broth may contain the usual additives, for instance other inorganic salts, such as $CoCl_2$, $MgCl_2$, precursors, etc., in aqueous medium. The nutrient concentrate added during the enrichment period may be similar in composition, but it may contain water only in an amount just necessary to dissolve the soluble components, since no fermentation broth is removed from the fermenter during the enrichment period, and thus it is not necessary to supplement the volume of the fermentation broth.

The main advantage of the process according to the invention is that it provides a simple, industrially well realizable and very economical method for increasing the vitamin $B_{12}$ concentration of about 10,000 mcg./l., attainable by the hitherto known fermentation processes performed under septic conditions with mixed mesophilic methane-producing bacterium populations, to about 30,000 to 40,000 mcg./l., and that this high concentration, not attainable so far with septic fermentation processes, can be maintained for any desired time in e.g. a semicontinous fermentation process. By removing greater daily amounts of the fermentation broth the production can be increased further. By removing greater amounts of fermentation broth with vitamin $B_{12}$ concentrations increased several times, the production of vitamin $B_{12}$ becomes substantially more economical.

The process of the invention is elucidated in detail by the aid of the following non-limiting Examples. The vitamin $B_{12}$ concentrations of the fermentation broth indicated in the Examples were determined according to the usual paper-chromatographic method. Before the analysis the bacterium cells in the fermentation broth were subjected to cell-lysis by boiling in a medium of pH 4.9 to 5.2, in the presence of $FeCl_3$ and NaCl.

EXAMPLE 1

9400 ml. of a fermentation broth containing 10,500 mcg./l. of vitamin $B_{12}$, produced by a known semicontinuous industrial fermentation utilizing a methane-producing mixed bacterium population, are introduced into a laboratory-scale fermenter with a working capacity of 10 l. The fermentation broth is heated to 28°–30°C, and a nutrient mixture of the following composition is added:

| | | |
|---|---|---|
| ammonium hydrocarbonate | 4.5 | g. |
| ammonium hydroxide (24 %) | 1.5 | ml. |
| diammonium hydrophosphate | 0.45 | g. |
| ammonium sulfate | 1.5 | g. |
| brewer's yeast extract (20%; dry material) content: 20–30%, total nitrogen | | |

| | | |
|---|---|---|
| content: 43–47%) | 1.0 | ml. |
| cobalt chloride | 0.010 | g. |
| succinic acid | 0.006 | g. |
| o-xylidine | 0.020 | g. |
| magnesium chloride | 0.1 | g. |
| methanol | 60.0 | ml. |
| water q.s. ad | 100.0 | ml. |

In this nutrient mixture the weight ratio of the inorganic ammonium nitrogen related to the methanol carbon is about 1:11.

Thereafter a mixture of 7.0 g. of corn steep liquor (dry material content: 55 to 60%, total nitrogen content: 3 to 4%) and 0.006 g. of 5,6-dimethylbenzimidazole is added to the broth.

After the introduction of the nutrients the fermentation broth is thoroughly mixed, and then the fermenter is covered with a rubber plate and placed into a thermovessel heated to 32° to 34°C. The broth is incubated at this temperature for 6 days, and during this period 100 ml. portions of a nutrient mixture with the above composition are added daily to the broth. Thus, on the seventh day of incubation the volume of the fermentation broth reaches 10 l. From this time on the fermentation is continued in semicontinuous manner, i.e. 10% of the fermentation broth is removed daily in a single portion for processing and replaced by the same volume of a fresh nutrient broth. The composition of the fresh nutrient broth should be adjusted so that the assimilable nitrogen and carbon removed with the separated portion of fermentation broth and in the form of methane is replaced completely.

The total nitrogen concentration of the removed fermentation broth (determined e.g. by the Kjeldahl method) is 2025 mg./l., consequently 2025 g. of nitrogen are removed from the fermenter with the separated 1 liter of fermentation broth. Thus the daily supplement of 1 liter of nutrient broth should contain about 2025 g. of nitrogen in the form of inorganic ammonium compounds, and about 12 times greater amount of carbon in the form of methanol. Accordingly, the tenth volume of fermentation broth, removed daily from the fermenter, is replaced by 1 liter of a fresh nutrient broth with the following composition:

| | | |
|---|---|---|
| ammonium hydrocarbonate | 6.0 | g. |
| ammonium hydroxide (24%) | 2.0 | ml. |
| diammonium hydrophosphate | 0.6 | g. |
| ammonium sulfate | 2.0 | g. |
| hydrolysed brewer's yeast (20%) | 1.0 | ml. |
| cobalt chloride | 0.025 | g. |
| succinic acid | 0.006 | g. |
| o-xylidine | 0.020 | g. |
| magnesium chloride | 0.1 | g. |
| Methanol 80 ml | | |
| water q.s. ad | 1000.0 | ml. |

In this nutrient broth the ratio of ammonium nitrogen and methanol carbon (g. N : g. C) is 1:12.

Furthermore, a mixture of 9 g. of corn steep liquor and 0.015 g. of 5,6-dimethylbenzimidazole (precursor) is added daily to the fermentation broth.

The removal of 1 liter of fermentation broth and the addition of 1 liter of nutrient broth with the above composition are repeated daily for any desired time. The portion of fermentation broth removed daily contains, with a negligible fluctuation, about 20,460 mcg./l. of vitamin $B_{12}$ and about 200 mg./l. of factor III, biologically equivalent with vitamin $B_{12}$. Accordingly, the vitamin $B_{12}$ production increases to 195% as compared to the initial value of 10,500 mcg./l.

EXAMPLE 2

930 ml. of a fermentation broth produced by a known semicontinuous industrial fermentation utilizing a methane-producing mixed mesophilic bacterium population are introduced into a laboratory-scale fermenter with a working capacity of 10 l., and, at a temperature of 28° to 30°C, a nutrient concentrate of the following composition is added:

| | | |
|---|---|---|
| ammonium hydrocarbonate | 0.6 | g. |
| ammonium hydroxide (24%) | 0.2 | g. |
| diammonium hydrophosphate | 0.06 | g. |
| ammonium sulfate | 0.2 | g. |
| hydrolyzed brewer's yeast (20%) | 0.1 | ml. |
| cobalt chloride | 0.001 | g. |
| succinic acid | 0.0006 | g. |
| o-xylidine | 0.002 | g. |
| magnesium chloride | 0.01 | g. |
| methanol | 9.0 | ml. |
| water q.s. ad | 10.0 | ml. |

In this nutrient concentrate the ratio of ammonium nitrogen and methanol carbon (g. N : g. C) is 1:13.

Furthermore, a mixture of 7.0 g. of corn steep liquor (dry material content: 55–60 %, total nitrogen content: 3–4%) and 0.006 g. of 5,6-dimethylbenzimidazole is added to the broth.

On the next 6 days one proceeds as described in Example 1 with the difference that 10 ml. portions of a nutrient concentrate with the above composition are added daily to the broth.

On the seventh day the semicontinuous fermentation is started as follows: The contents of the fermenter is thoroughly homogenized, and then 10% of the fermentation broth is removed. The nitrogen and carbon contents of the removed broth, determined by analysis, are 2570 mg./l. of N and 8640 mg./l. of C, respectively. Thereafter, at 28° to 30°C, the same volume (i.e. 1 liter) of a fresh nutrient medium with a composition of

| | | |
|---|---|---|
| ammonium hydrocarbonate | 0.6 | g. |
| ammonium hydroxide (24 %) | 0.2 | g. |
| diammonium phosphate | 0.06 | g. |
| ammonium sulfate | 0.2 | g. |
| hydrolyzed brewer's yeast (20%) | 0.1 | ml. |
| cobalt chloride | 0.001 | g. |
| succinic acid | 0.0006 | g. |
| o-xylidine | 0.002 | g. |
| magnesium chloride | 0.01 | g. |
| methanol | 10.0 | ml. |
| water q.s. ad | 100.0 | ml. | is added to the broth. In this nutrient medium the ratio of ammonium nitrogen and methanol carbon (g. N : g. C) is 1:14.

Furthermore, a mixture of 0.9 g. of corn steep liquor and 0.0015 g. of 5,6-dimethylbenzimidazole (precursor) is added daily to the broth.

The removal of 1 liter of fermentation broth and the addition of 1 liter of nutrient broth with the above composition are repeated daily for 7 days. The portion of fermentation broth removed daily contains, with a negligible fluctuation, about 24,200 mcg./l. of vitamin $B_{12}$ and about 200 $\mu$./l. of factor III, biologically equivalent with vitamin $B_{12}$. Accordingly, the vitamin $B_{12}$ production increases to 215% as compared to the initial value of 11,250 mcg./l.

EXAMPLE 3

9300 ml. of a fermentation broth containing 10,640 mcg./l. of vitamin $B_{12}$, produced by a known semicontinuous industrial fermentation utilizing a methane-producing mixed mesophilic bacterium population, are introduced into a glass fermenter with a capacity of 10 l., and, at a temperature of 28° to 30°C, a nutrient concentrate of the following composition is added:

| | | |
|---|---|---|
| ammonium hydrocarbonate | 6.0 | g. |
| ammonium hydroxide (24 %) | 2.0 | ml. |
| diammonium hydrophosphate | 0.6 | g. |
| ammonium sulfate | 2.0 | g. |
| hydrolyzed brewer's yeast (20%) | 1.0 | ml. |
| cobalt chloride | 0.01 | g. |
| succinic acid | 0.006 | g. |
| o-xylidine | 0.02 | g. |
| magnesium chloride | 0.1 | g. |
| methanol | 90.0 | ml. |
| water q.s. ad | 100.0 | ml. |

In this nutrient concentrate the ratio of ammonium nitrogen and methanol carbon (g. N : g. C) is 1:13.

Furthermore, a mixture of 9 g. of corn steep liquor (dry material: 55–60%, total nitrogen content: 3–4%) and 0.006 g. of 5,6-dimethylbenzimidazole is added to the broth.

On the next 6 days one proceeds as described in Example 1, with the difference that 10 ml. portions of a nutrient concentrate with the above composition are added daily to the broth.

On the seventh day the semicontinuous fermentation is started as follows:

The content of the fermenter is thoroughly homogenized, and then 10% of the fermentation broth is removed. The nitrogen and carbon contents of the removed broth, determined by analysis, are 2755 mg./l. of N and 8125 mg./l. of C, respectively. Thereafter, at 28° to 30°C, the same volume (i.e. 1 liter) of a fresh nutrient broth with a composition of

| | | |
|---|---|---|
| ammonium hydrocarbonate | 6.0 | g. |
| ammonium hydroxide (24%) | 2.0 | ml. |
| diammonium hydrophosphate | 0.6 | g. |
| ammonium sulfate | 2.0 | g. |
| hydrolyzed brewer's yeast (20%) | 1.0 | ml. |
| cobalt chloride | 0.025 | g. |
| succinic acid | 0.006 | g. |
| o-xylidine | 0.02 | g. |
| magnesium chloride | 0.1 | g. |
| methanol | 100.0 | ml. |
| water q.s. ad | 1000.0 | ml. | is added to the broth. In this nutrient medium the ratio of ammonium nitrogen and methanol carbon (g. N : g. C) is 1:14.

Furthermore, a mixture of 9 g. of corn steep liquor (dry material: 55–60%, total nitrogen content: 3–4%) and 0.015 g. of 5,6-dimethylbenzimidazole is added to the broth.

The removal of 1 liter of fermentation broth and the addition of 1 liter of nutrient broth with the above composition is repeated daily for 6 days. On the seventh day the fermentation broth is sampled and analyzed for vitamin $B_{12}$ and factor III. The following results are obtained: vitamin $B_{12}$ = 25,870 mcg./l., factor III = = 6060 mcg./l.

Accordingly, the vitamin $B_{12}$ production increases to 249% as compared to the initial value.

EXAMPLE 4

40 m$^3$. of a fermentation broth containing 11,950 mcg./l. of vitamin $B_{12}$, produced by a known semicontinuous industrial fermentation utilizing a methane-producing mixed mesophilic bacterium population, are introduced into a plant fermenter with a capacity of 70 m$^3$., and, at a temperature of 28° to 30°C, a nutrient medium with the following composition is added:

| | | |
|---|---|---|
| ammonium hydrocarbonate | 15.0 | kg. |
| ammonium hydroxide (24%) | 5.0 | kg. |
| diammonium hydrophosphate | 1.5 | kg. |
| ammonium sulfate | 8.0 | kg. |
| hydrolyzed brewer's yeast (20%) | 5.0 | kg. |
| cobalt chloride | 50.0 | g. |
| succinic acid | 30.0 | g. |
| o-xylidine | 100.0 | g. |
| magnesium chloride | 500.0 | g. |
| methanol | 450.0 | l. |
| water q.s. ad | 2 | m$^3$. |

In this nutrient medium the ratio of ammonium nitrogen and methanol carbon (g. N : g. C) is 1:13.

Furthermore, a mixture of 24 kg. of corn steep liquor (dry material: 55–60%, total nitrogen content: 3–4%) and 30 kg. of 5,6-dimethylbenzimidazole is added to the broth.

On the next 6 days one proceeds as described in Example 1, with the difference that 2 m$^3$. portions of a nutrient broth with the above composition are added daily to the broth.

On the seventh day the semicontinuous fermentation is started as follows:

10% of the fermentation broth is removed. The nitrogen and carbon contents of the removed broth, determined by analysis, are 2250 mg./l. of N and 8270 mg./l. of C, respectively. Accordingly, the same volume of a fresh nutrient medium with a composition of

| | | |
|---|---|---|
| ammonium hydrocarbonate | 30.0 | kg. |
| ammonium hydroxide (24%) | 10.0 | kg. |
| diammonium hydrophosphate | 2.0 | kg. |
| ammonium sulfate | 15.0 | kg. |
| hydrolyzed brewer's yeast (20%) | 5.0 | kg. |
| cobalt chloride | 100.0 | g. |
| succinic acid | 30.0 | g. |
| o-xylidine | 100.0 | g. |
| magnesium chloride | 500.0 | g. |
| methanol | 500.0 | l. |
| water q.s. | | | is added to the broth. In this nutrient medium the ratio of ammonium nitrogen and methanol carbon (g. N : g. C.) is 1:14.

Furthermore, a mixture of 24 kg. of corn steep liquor (dry material: 55–60%, total nitrogen content: 3–4%) and 60 kg. of 5,6-dimethylbenzimidazole is added to the broth.

Thereafter one proceeds as described in Example 1. On the seventh day the fermentation broth is sampled and analysed for vitamin $B_{12}$. According to the analysis the vitamin $B_{12}$ content of the broth is 25,950 mcg./l., the total amount of vitamin $B_{12}$ and factor III is 33,650 mcg./l. Thus, the vitamin $B_{12}$ production increases to 217% as compared to the initial value.

EXAMPLE 5

9000 ml. of a fermentation broth containing 11,870 mcg./l. of vitamin $B_{12}$, produced by a known fermentation utilizing a methane-producing mixed mesophilic bacterium population, are introduced into a glass fermenter with a capacity of 10 l., and, at a temperature of 28° to 30°C, a nutrient concentrate with the following composition is added:

| | | |
|---|---|---|
| ammonium hydrocarbonate | 6.0 | g. |
| ammonium hydroxide (24%) | 2.0 | ml. |
| diammonium hydrophosphate | 0.6 | g. |
| ammonium sulfate | 2.0 | g. |
| hydrolyzed brewer's yeast (20%) | 1.0 | ml. |
| cobalt chloride | 0.01 | g. |
| succinic acid | 0.006 | g. |
| o-xylidine | 0.02 | g. |
| magnesium chloride | 0.1 | g. |
| methanol | 90.0 | ml. |
| water q.s. ad | 100.0 | ml. |

In this nutrient concentrate the ratio of ammonium nitrogen and methanol carbon (g. N : g. C) is 1:14.

Furthermore, a mixture of 9 g. of corn steep liquor (dry material: 55–60%, total nitrogen content: 3–4%) and 0.006 g. of 5,6-dimethylbenzimidazole is added to the broth.

On the next 8 days one proceeds as described in Example 1, with the difference that 10 ml. portions of a nutrient concentrate with the above composition are added daily to the broth.

On the ninth day the semicontinuous fermentation is started as follows:

10% of the fermentation broth is removed. The nitrogen and carbon contents of the removed broth, determined by analysis, are 3254 mg./l. of N and 10,520 mg./l. of C, respectively. Thereafter, at 28° to 30°C, the same volume (i.e. 1 liter) of a fresh nutrient broth with a composition of

| | | |
|---|---|---|
| ammonium hydrocarbonate | 7.5 | g. |
| ammonium hydroxide (24%) | 2.5 | ml. |
| diammonium hydrophosphate | 0.75 | g. |
| ammonium sulfate | 2.5 | g. |
| hydrolyzed brewer's yeast (20%) | 1.0 | ml. |
| cobalt chloride | 0.025 | g. |
| succinic acid | 0.006 | g. |
| o-xylidine | 0.02 | g. |
| magnesium chloride | 0.1 | g. |
| methanol | 120.0 | ml. |
| water q.s. ad | 1000.0 | ml. | is added to the broth. In the nutrient medium the ratio of ammonium nitrogen and methanol carbon (g. N : g. C) is 1:15.

Furthermore, a mixture of 10 g. of corn steep liquor (dry material: 55–60%, total nitrogen content: 3–4%) and 0.015 g. of 5,6-dimethylbenzimidazole is added to the broth.

Thereafter one proceeds as described in Example 1. On the ninth day the fermentation broth is sampled and analyzed for vitamin $B_{12}$. According to the analysis, the vitamin $B_{12}$ content of the broth is 34,650 mcg./l., the total amount of vitamin $B_{12}$ and factor III, biologically equivalent with vitamin $B_{12}$, is 41,320 mcg./l. Thus the vitamin $B_{12}$ production increases to 300.2 % as compared to the initial value.

EXAMPLE 6

9000 ml. of a fermentation broth containing 11,870 mcg./l. of vitamin $B_{12}$, produced by a fermentation performed with a methane-producing mixed mesophilic bacterium population, are introduced into a glass fermenter with a capacity of 10 l. Thereafter a nutrient broth concentrate and a mixture of corn steep liquor concentrate and 5,6-dimethylbenzimidazole, each with the same composition as given in Example 5, are introduced daily once for 9 days. On the ninth day the concentration of vitamin $B_{12}$ in the fermentation broth reaches the value of 35,000 mcg./l. At this point a semicontinuous fermentation is started as described in Example 5, and this procedure is continued in the same manner for 2 weeks. According to the analysis of the one-tenth portions of fermentation broth removed daily, the vitamin $B_{12}$ concentration of the broth remains steadily 35,000 mcg./l.

At the end of this period 10% portions of the fermentation broth are removed twice a day, in 12 hours, intervals, and replaced by equal volumes (i.e. 1 liter) of fresh nutrient medium with the composition given in Example 5. This phase of fermentation is continued for further three weeks. The fermentation broth removed daily shows a steady vitamin $B_{12}$ concentration of 34,500 mcg./l. in average; if the amount of the biologically equivalent factor III is also included, a concentration of 43,470 mcg./l. is reached. Thus the increase in vitamin $B_{12}$ concentration is 290% as compared to the initial value.

EXAMPLE 7

One proceeds as described in Example 6 with the only difference that in the third stage (i.e. when fermentation broth is removed twice a day) only a half of the nutrient medium is added to the broth in the second instance.

Under such conditions the vitamin $B_{12}$ content of the fermentation broth removed daily is 26,000 mcg./l. on the average, corresponding to an increase of 220%.

What we claim is:

1. A method of increasing Vitamin $B_{12}$ production in a fermentation broth undergoing fermentation to produce Vitamin $B_{12}$ and containing a mixed population of a mesophilic methane-producing bacteria under anaerobic conditions which comprises the following steps:

a. adding daily to said fermentation broth, for a period of from 4 to 7 days, a first, broth-enriching nutrient concentrate containing at least 90% of the total amount of nitrogen source in the form of inorganic ammonium compounds and at least 90% of the total amount of a carbon source in the form of methanol and having an N:C weight ratio of 1:11 to 1:15 to increase the total concentration of assimilable nitrogen in the broth by a factor of maximum 4; and b. periodically removing an effective portion of the fermentation broth and replacing same with an equal fresh portion of a second, broth-enriching nutrient concentrate also containing at least 90% of the total amount of a nitrogen source in the form of inorganic ammonium compounds and at least 90% of the total amount of a carbon source in the form of methanol and having an N:C weight ratio of 1:11 to 1:15 wherein the weight ratio of methanol carbon to ammonia nitrogen is 6 to 10% higher than that in the first nutrient concentrate added in step (a).

* * * * *